(12) United States Patent
Peter et al.

(10) Patent No.: US 9,260,747 B2
(45) Date of Patent: Feb. 16, 2016

(54) ANALYSIS OF SINGLE NUCLEOTIDE POLYMORPHISMS USING END LABELING

(75) Inventors: Brian J. Peter, Los Altos, CA (US); Nicholas M. Sampas, San Jose, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 1197 days.

(21) Appl. No.: 12/758,713

(22) Filed: Apr. 12, 2010

(65) Prior Publication Data

US 2011/0250595 A1  Oct. 13, 2011

(51) Int. Cl.
*C12Q 1/68* (2006.01)
*G01N 33/53* (2006.01)
*C12M 1/34* (2006.01)

(52) U.S. Cl.
CPC .............. *C12Q 1/683* (2013.01); *C12Q 1/6837* (2013.01)

(58) Field of Classification Search
CPC ........... C12Q 1/6837; C12Q 2565/501; C12Q 2525/191; C12Q 2521/301
See application file for complete search history.

(56) References Cited

U.S. PATENT DOCUMENTS

2007/0128650 A1  6/2007  Schell et al.
2009/0035762 A1*  2/2009  Sampas ............................ 435/6

OTHER PUBLICATIONS

Roth et al (nature Biotechnology (2004) vol. 22, pp. 418-426).*
Kilian, et al. The fast and the cheap: SNP and DArT-based whole genome profiling for crop improvement. In the Wake of the Double Helix: From the Green Revolution to the Gene Revolution. Edited by: Tuberosa R, Phillips RL, Gale M. Bologna, Italy: Avenue media; 2005:443-461.
Wenzl, et al. Diversity arrays technology (DArT) for whole-genome profiling of barley. PNAS. 2004, vol. 101, No. 26, pp. 9915-9920.

* cited by examiner

*Primary Examiner* — Steven Pohnert

(57) ABSTRACT

A method for analyzing a sequence comprising a SNP site is provide. In general terms, the method comprises: a) contacting a first DNA sample with a first restriction enzyme to provide DNA fragments, wherein: i) the first restriction enzyme cleaves the sequence only if a first allele of a SNP is present at the SNP site; b) end-labeling the DNA fragments to produce an end-labeled sample; c) hybridizing the end-labeled sample to an array comprising a probe sequence; and d) comparing the amount of hybridization between the digested sample and the probe sequence to a reference signal.

19 Claims, 5 Drawing Sheets

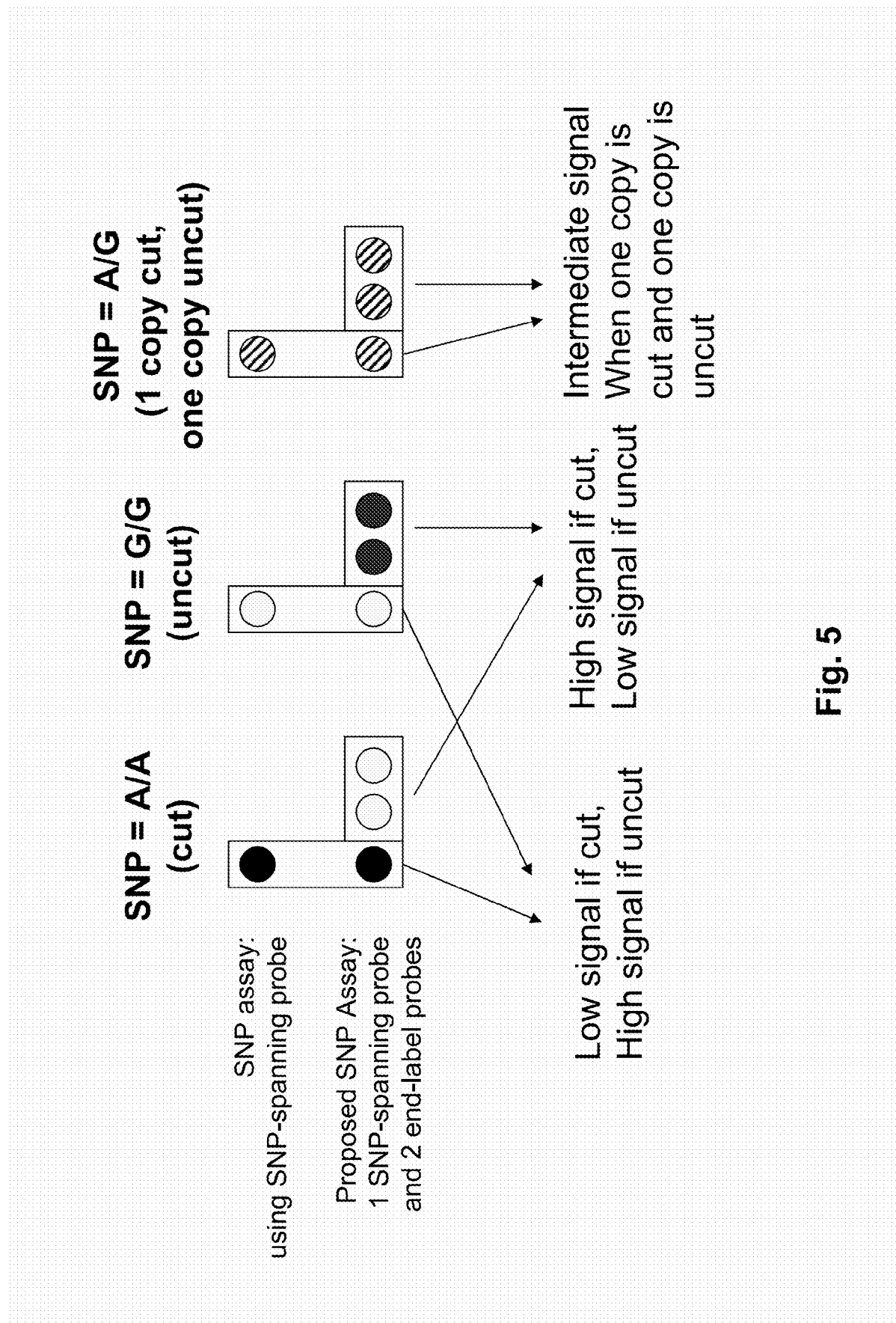

SEQUENCE LISTING

<160> NUMBER OF SEQ ID NOS: 23

<210> SEQ ID NO 1
<211> LENGTH: 4
<212> TYPE: DNA
<213> ORGANISM: Artificial Sequence
<220> FEATURE:
<223> OTHER INFORMATION: Synthetic oligonucleotide

<400> SEQUENCE: 1 gtac                                                                      4

<210> SEQ ID NO 2
<211> LENGTH: 8
<212> TYPE: DNA
<213> ORGANISM: Artificial Sequence
<220> FEATURE:
<223> OTHER INFORMATION: Synthetic oligonucleotide

<400> SEQUENCE: 2 attataac                                                                  8

<210> SEQ ID NO 3
<211> LENGTH: 8
<212> TYPE: DNA
<213> ORGANISM: Artificial Sequence
<220> FEATURE:
<223> OTHER INFORMATION: Synthetic oligonucleotide

<400> SEQUENCE: 3 attatatg                                                                  8

<210> SEQ ID NO 4
<211> LENGTH: 8
<212> TYPE: DNA
<213> ORGANISM: Artificial Sequence
<220> FEATURE:
<223> OTHER INFORMATION: Synthetic oligonucleotide

<400> SEQUENCE: 4 gtatatta                                                                  8

<210> SEQ ID NO 5
<211> LENGTH: 8
<212> TYPE: DNA
<213> ORGANISM: Artificial Sequence
<220> FEATURE:
<223> OTHER INFORMATION: Synthetic oligonucleotide

<400> SEQUENCE: 5 taatatac                                                                  8

<210> SEQ ID NO 6
<211> LENGTH: 8
<212> TYPE: DNA
<213> ORGANISM: Artificial Sequence
<220> FEATURE:
<223> OTHER INFORMATION: Synthetic oligonucleotide

<400> SEQUENCE: 6 gttataat                                                                  8

<210> SEQ ID NO 7
<211> LENGTH: 4
<212> TYPE: DNA
<213> ORGANISM: Artificial Sequence

```
<220> FEATURE:
<223> OTHER INFORMATION: Synthetic oligonucleotide

<400> SEQUENCE: 7 gtgc                                                                  4

<210> SEQ ID NO 8
<211> LENGTH: 8
<212> TYPE: DNA
<213> ORGANISM: Artificial Sequence
<220> FEATURE:
<223> OTHER INFORMATION: Synthetic oligonucleotide

<400> SEQUENCE: 8 attataac                                                              8

<210> SEQ ID NO 9
<211> LENGTH: 8
<212> TYPE: DNA
<213> ORGANISM: Artificial Sequence
<220> FEATURE:
<223> OTHER INFORMATION: Synthetic oligonucleotide

<400> SEQUENCE: 9 gttataat                                                              8

<210> SEQ ID NO 10
<211> LENGTH: 4
<212> TYPE: DNA
<213> ORGANISM: Artificial Sequence
<220> FEATURE:
<223> OTHER INFORMATION: Synthetic oligonucleotide

<400> SEQUENCE: 10 gtgc                                                                  4

<210> SEQ ID NO 11
<211> LENGTH: 4
<212> TYPE: DNA
<213> ORGANISM: Artificial Sequence
<220> FEATURE:
<223> OTHER INFORMATION: Synthetic oligonucleotide

<400> SEQUENCE: 11 gtcc                                                                  4

<210> SEQ ID NO 12
<211> LENGTH: 8
<212> TYPE: DNA
<213> ORGANISM: Artificial Sequence
<220> FEATURE:
<223> OTHER INFORMATION: Synthetic oligonucleotide

<400> SEQUENCE: 12 cttataat                                                              8

<210> SEQ ID NO 13
<211> LENGTH: 59
<212> TYPE: DNA
<213> ORGANISM: Artificial Sequence
<220> FEATURE:
<223> OTHER INFORMATION: Synthetic oligonucleotide

<400> SEQUENCE: 13
ctcaggcaag aaaatcatat caaaaagcaa caagtttaca aaaatagaaa ataattaca     59
```

<210> SEQ ID NO 14
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 14
ctcaggcaag aaaatcatat caaaaagc                                28

<210> SEQ ID NO 15
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 15
atcaagttta caaaaataga aaataattac a                             31

<210> SEQ ID NO 16
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 16
tatattatca ca                                                  12

<210> SEQ ID NO 17
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 17
tgtgataata ta                                                  12

<210> SEQ ID NO 18
<211> LENGTH: 59
<212> TYPE: DNA
<213> ORGANISM: Artificial Sequence
<220> FEATURE:
<223> OTHER INFORMATION: Synthetic oligonucleotide

<400> SEQUENCE: 18
ctcaggcaag aaaatcatat caaaaagcaa caagtttaca aaaatagaaa ataattaca    59

<210> SEQ ID NO 19
<211> LENGTH: 59
<212> TYPE: DNA
<213> ORGANISM: Artificial Sequence
<220> FEATURE:
<223> OTHER INFORMATION: Synthetic oligonucleotide

<400> SEQUENCE: 19
tgtaattatt ttctattttt gtaaacttgt tgcttttga tatgattttc ttgcctgag     59

<210> SEQ ID NO 20
<211> LENGTH: 40
<212> TYPE: DNA
<213> ORGANISM: Artificial Sequence
<220> FEATURE:
<223> OTHER INFORMATION: Synthetic oligonucleotide

```
<400> SEQUENCE: 20
ctcaggcaag aaaatcatat caaaaagcta tattatcaca                              40

<210> SEQ ID NO 21
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 21
tgtgataata tagcttttg atatgatttt cttgcctgag                               40

<210> SEQ ID NO 22
<211> LENGTH: 43
<212> TYPE: DNA
<213> ORGANISM: Artificial Sequence
<220> FEATURE:
<223> OTHER INFORMATION: Synthetic oligonucleotide

<400> SEQUENCE: 22
tgtgataata taatcaagtt tacaaaaata gaaaataatt aca                          43

<210> SEQ ID NO 23
<211> LENGTH: 43
<212> TYPE: DNA
<213> ORGANISM: Artificial Sequence
<220> FEATURE:
<223> OTHER INFORMATION: Synthetic oligonucleotide

<400> SEQUENCE: 23
tgtaattatt ttctattttt gtaaacttgt ttatattatc aca                          43
```

ANALYSIS OF SINGLE NUCLEOTIDE POLYMORPHISMS USING END LABELING

INTRODUCTION

The human genome has several types of variation which confer genetic differences between individuals. Single nucleotide polymorphisms (SNPs) are sites of single base changes which vary in at least 1% of the population. Copy number variants (CNVs) are larger regions of DNA which are duplicated or deleted with respect to a reference genome.

Methods for the determination of SNP alleles and copy number measurements are important to the research community for the diagnosis of disease, especially in cytogenetics and cancer. Researchers could benefit from the development of a high throughput means for analyzing SNPs in human genomic DNA.

BRIEF DESCRIPTION OF THE FIGURES

FIG. 5 provides prophetic results obtained using the instant method in combination with the method schematically illustrated in FIG. 4.

DEFINITIONS

Figure 1:
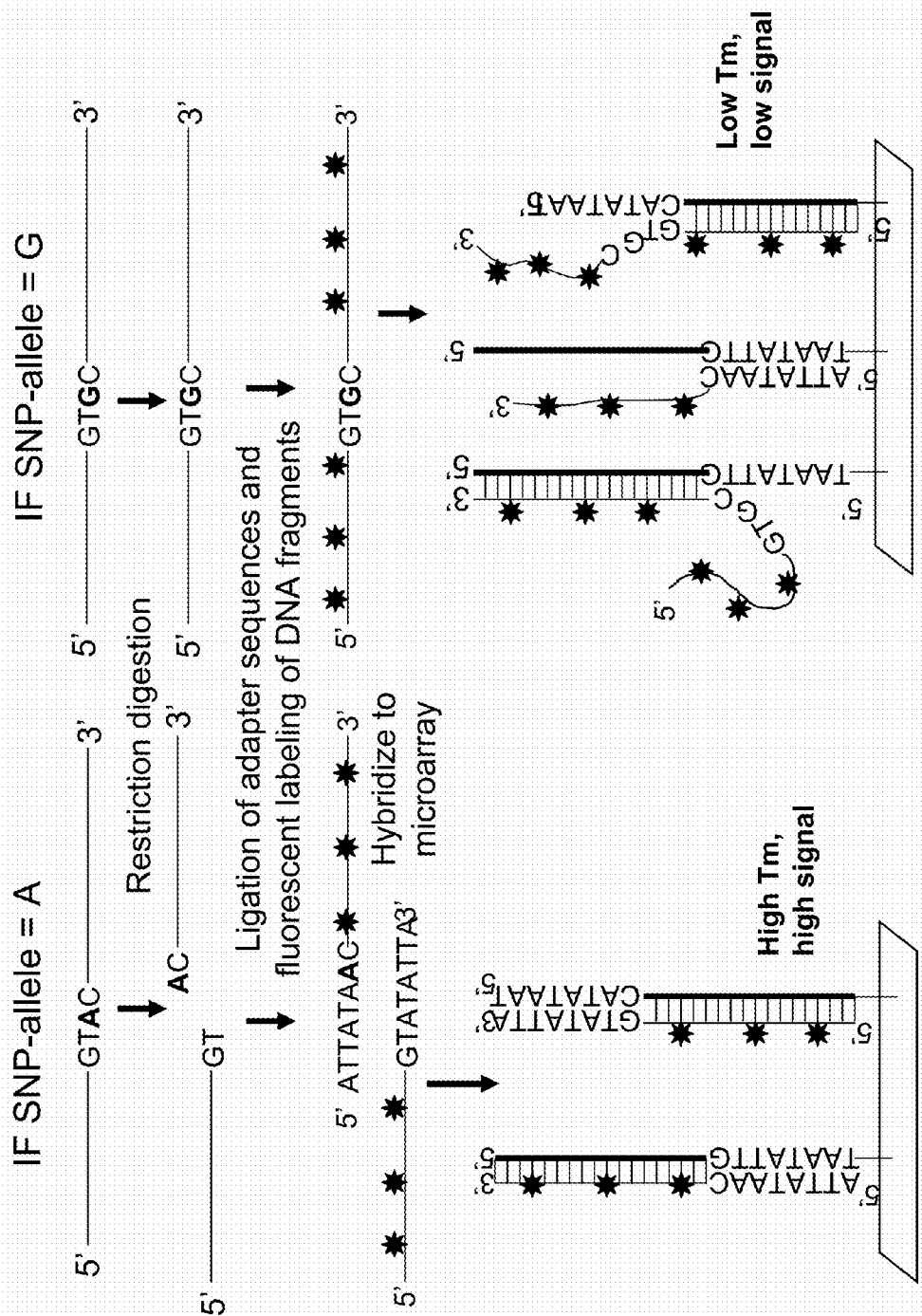
FIG. 1 schematically illustrates one embodiment in which the allele of a SNP is detected by ligating an adaptor to a restriction enzyme cleavage site (SEQ ID NOS: 1-12)

The term "sample", as used herein, relates to a material or mixture of materials, typically, although not necessarily, in liquid form, containing one or more analytes of interest.

The term "genome", as used herein, relates to a material or mixture of materials, containing genetic material from an organism. The term "genomic DNA" as used herein refers to deoxyribonucleic acids that are obtained from an organism. The term "genomic DNA" as used herein also encompasses deoxyribonucleic acids that derived from nucleic acids obtained from an organism, for example, cDNA derived from RNA obtained from an organism. The terms "genome" and "genomic DNA" encompass genetic material that may have undergone amplification, purification, or fragmentation. In some cases, genomic DNA encompasses nucleic acids isolated from a single cell, or a small number of cells. The "genome" in the sample that is of interest in a study may encompass the entirety of the genetic material from an organism, or it may encompass only a selected fraction thereof: for example, a genome may encompass one chromosome from an organism with a plurality of chromosomes.

The term "genomic region" or "genomic segment", as used herein, denotes a contiguous length of nucleotides in a genome of an organism.

The term "reference," as used herein refers to a genome, a genomic region, or a nucleotide acid to which a sample may be compared. In certain cases, the reference contains a region of known nucleotide sequence, e.g. a chromosomal region whose sequence is deposited at NCBI's Genbank database or other databases, for example. The reference may be the same species (e.g., where the species is human, or mouse, for example) as that of the sample analyzed in the subject method. The reference sample may represent the genome of an individual, or may represent either a physical pooling of the genomes of multiple individual or computational combination of the signals or ratios of signals from a number of individuals. A "reference sample" includes one or more samples that have been run earlier than a test sample, where data from the reference sample is processed to provide an estimate of what to expect if a test sample is heterozygous or homozygous for an allele of a SNP.

The term "nucleotide" is intended to include those moieties that contain not only the known purine and pyrimidine bases, but also other heterocyclic bases that have been modified. Such modifications include methylated purines or pyrimidines, acylated purines or pyrimidines, alkylated riboses or other heterocycles. In addition, the term "nucleotide" includes those moieties that contain hapten or fluorescent labels and may contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, are functionalized as ethers, amines, or the likes. Nucleotides may include those that when incorporated into an extending strand of a nucleic acid enables continued extension (non-chain terminating nucleotides) and those that prevent subsequent extension (e.g. chain terminators).

The term "nucleic acid" and "polynucleotide" are used interchangeably herein to describe a polymer of any length, e.g., greater than about 2 bases, greater than about 10 bases, greater than about 100 bases, greater than about 500 bases, greater than 1000 bases, up to about 10,000 or more bases composed of nucleotides, e.g., deoxyribonucleotides or ribonucleotides, and may be produced enzymatically or synthetically (e.g., PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions. Naturally-occurring nucleotides include guanine, cytosine, adenine and thymine (G, C, A and T, respectively).

The term "oligonucleotide", as used herein, denotes a single-stranded multimer of nucleotides from about 2 to 500 nucleotides, e.g., 2 to 200 nucleotides. Oligonucleotides may be synthetic or may be made enzymatically, and, in some embodiments, are under 10 to 50 nucleotides in length. Oligonucleotides may contain ribonucleotide monomers (i.e., may be oligoribonucleotides) or deoxyribonucleotide monomers. Oligonucleotides may be 10 to 20, 11 to 30, 31 to 40, 41 to 50, 51-60, 61 to 70, 71 to 80, 80 to 100, 100 to 150 or 150 to 200, up to 500 or more nucleotides in length, for example.

The term "duplex" or "double-stranded" as used herein refers to nucleic acids formed by hybridization of two single strands of nucleic acids containing complementary sequences. In most cases, genomic DNA is double-stranded.

The term "complementary" as used herein refers to a nucleotide sequence that base-pairs by non-covalent bonds to a target nucleic acid of interest. In the canonical Watson-Crick base pairing, adenine (A) forms a base pair with thymine (T), as does guanine (G) with cytosine (C) in DNA. In RNA, thymine is replaced by uracil (U). As such, A is complementary to T and G is complementary to C. In RNA, A is complementary to U and vice versa. Typically, "complementary" refers to a nucleotide sequence that is at least partially complementary. The term "complementary" may also encompass duplexes that are fully complementary such that every nucleotide in one strand is complementary to every nucleotide in the other strand in corresponding positions. In certain cases, a nucleotide sequence may be partially complementary to a target, in which not all nucleotide is complementary to every nucleotide in the target nucleic acid in all the corresponding positions.

The term "probe," as used herein, refers to a nucleic acid that is complementary to a nucleotide sequence of interest. In certain cases, detection of a target analyte requires hybridization of a probe to a target. In certain embodiments, a probe may be immobilized on a surface of a substrate, where the substrate can have a variety of configurations, e.g., a sheet, bead, or other structure. In certain embodiments, a probe may be present on a surface of a planar support, e.g., in the form of an array.

An "array," includes any two-dimensional or substantially two-dimensional (as well as a three-dimensional) arrangement of addressable regions, e.g., spatially addressable regions or optically addressable regions, bearing nucleic acids, particularly oligonucleotides or synthetic mimetics thereof, and the like. In some cases, the addressable regions of the array may not be physically connected to one another, for example, a plurality of beads that are distinguishable by optical or other means may constitute an array. Where the arrays are arrays of nucleic acids, the nucleic acids may be adsorbed, physisorbed, chemisorbed, or covalently attached to the arrays at any point or points along the nucleic acid chain.

Any given substrate may carry one, two, four or more arrays disposed on a surface of the substrate. Depending upon the use, any or all of the arrays may be the same or different from one another and each may contain multiple spots or features. An array may contain one or more, including more than two, more than ten, more than one hundred, more than one thousand, more ten thousand features, or even more than one hundred thousand features, in an area of less than 20 cm$^2$ or even less than 10 cm$^2$, e.g., less than about 5 cm$^2$, including less than about 1 cm$^2$, less than about 1 mm$^2$, e.g., 100 µm$^2$, or even smaller. For example, features may have widths (that is, diameter, for a round spot) in the range from a 5 µm to 1.0 cm. In other embodiments each feature may have a width in the range of 1.0 µm to 1.0 mm, usually 5.0 µm to 500 µm, and more usually 10 µm to 200 µm. Non-round features may have area ranges equivalent to that of circular features with the foregoing width (diameter) ranges. At least some, or all, of the features are of different compositions (for example, when any repeats of each feature composition are excluded the remaining features may account for at least 5%, 10%, 20%, 50%, 95%, 99% or 100% of the total number of features). Inter-feature areas will typically (but not essentially) be present which do not carry any nucleic acids (or other biopolymer or chemical moiety of a type of which the features are composed). Such inter-feature areas typically will be present where the arrays are formed by processes involving drop deposition of reagents but may not be present when, for example, photolithographic array fabrication processes are used. It will be appreciated though, that the inter-feature areas, when present, could be of various sizes and configurations.

Each array may cover an area of less than 200 cm$^2$, or even less than 50 cm$^2$, 5 cm$^2$, 1 cm$^2$, 0.5 cm$^2$, or 0.1 cm$^2$. In certain embodiments, the substrate carrying the one or more arrays will be shaped generally as a rectangular solid (although other shapes are possible), having a length of more than 4 mm and less than 150 mm, usually more than 4 mm and less than 80 mm, more usually less than 20 mm; a width of more than 4 mm and less than 150 mm, usually less than 80 mm and more usually less than 20 mm; and a thickness of more than 0.01 mm and less than 5.0 mm, usually more than 0.1 mm and less than 2 mm and more usually more than 0.2 mm and less than 1.5 mm, such as more than about 0.8 mm and less than about 1.2 mm.

Arrays can be fabricated using drop deposition from pulse-jets of either precursor units (such as nucleotide or amino acid monomers) in the case of in situ fabrication, or the previously obtained nucleic acid. Such methods are described in detail in, for example, the previously cited references including U.S. Pat. Nos. 6,242,266, 232,072, 6,180,351, 6,171,797, 6,323,043, U.S. Patent Application Publication No. 20040203138 by Caren et al., and the references cited therein. As already mentioned, these references are incorporated herein by reference. Other drop deposition methods can be used for fabrication, as previously described herein. Also, instead of drop deposition methods, photolithographic array fabrication methods may be used. Inter-feature areas need not be present particularly when the arrays are made by photolithographic methods as described in those patents.

Arrays may also be made by distributing pre-synthesized nucleic acids linked to beads, also termed microspheres, onto a solid support. In certain embodiments, unique optical signatures are incorporated into the beads, e.g. fluorescent dyes, that could be used to identify the chemical functionality on any particular bead. Since the beads are first coded with an optical signature, the array may be decoded later, such that correlation of the location of an individual site on the array with the probe at that particular site may be made after the array has been made. Such methods are described in detail in, for example, U.S. Pat. Nos. 6,355,431, 7,033,754, and 7,060,431.

An array is "addressable" when it has multiple regions of different moieties (e.g., different oligonucleotide sequences) such that a region (i.e., a "feature" or "spot" of the array) at a particular predetermined location (i.e., an "address") on the array contains a particular sequence. Array features are typically, but need not be, separated by intervening spaces. An array is also "addressable" if the features of the array each have an optically detectable signature that identifies the moiety present at that feature. An array is also "addressable" if the features of the array each have a signature, which is detectable by non-optical means, that identifies the moiety present at that feature.

The terms "determining", "measuring", "evaluating", "assessing", "analyzing", and "assaying" are used interchangeably herein to refer to any form of measurement, and include determining if an element is present or not. These terms include both quantitative and/or qualitative determinations. Assessing may be relative or absolute. "Assessing the presence of" includes determining the amount of something present, as well as determining whether it is present or absent.

The term "using" has its conventional meaning, and, as such, means employing, e.g., putting into service, a method or composition to attain an end. For example, if a program is used to create a file, a program is executed to make a file, the file usually being the output of the program. In another example, if a computer file is used, it is usually accessed, read, and the information stored in the file employed to attain an end. Similarly if a unique identifier, e.g., a barcode is used, the unique identifier is usually read to identify, for example, an object or file associated with the unique identifier.

As used herein, the term "$T_m$" refers to the melting temperature an oligonucleotide duplex at which half of the duplexes remain hybridized and half of the duplexes dissociate into single strands. The $T_m$ of an oligonucleotide duplex may be experimentally determined or predicted using the following formula $T_m = 81.5 + 16.6(\log_{10}[Na^+]) + 0.41$ (fraction G+C)−(60/N), where N is the chain length and [Na$^+$] is less than 1 M. See Sambrook and Russell (2001; Molecular Cloning: A Laboratory Manual, 3$^{rd}$ ed., Cold Spring Harbor Press, Cold Spring Harbor N.Y., ch. 10). Other formulas for predicting T$_m$ of oligonucleotide duplexes may also be used depending on various hybridization conditions.

As used herein, the term "T$_m$-matched" refers to a plurality of nucleic acid duplexes having T$_m$s that are within a defined range, e.g. ±5° C., ±10° C., or ±15° C.

The term "hybridization conditions" as used herein refers to hybridization conditions that are optimized to anneal an oligonucleotide of a sufficient length to a probe, e.g. an oligonucleotide that is not nicked and has a contiguous length of at least 20 nucleotides (e.g. at least 30, at least 40, up to at least 50 or more) complementary to a nucleotide sequence of the probe. The hybridization conditions provide for dissociation of duplexes that anneal over a short length of region (e.g. less than 50, less than 40, less than 30, or less than 20 contiguous nucleotides) but not dissociation of duplexes formed between an un-nicked strand and its respective probe. Such conditions may differ from one experiment to the next depending on the length and the nucleotide content of the complementary region. In certain cases, the temperature for low-stringency hybridization is 5°-10° C. lower than the calculated T$_m$ of the resulting duplex under the conditions used. Details on the hybridization conditions suitable for use in certain embodiments in the present disclosure may be found in US Patent Publication 20090035762, the disclosure of which is incorporated herein by reference.

The term "homozygous" denotes a genetic condition in which identical alleles reside at the same loci on homologous chromosomes. In contrast, "heterozygous" denotes a genetic condition in which different alleles reside at the same loci on homologous chromosomes.

"Color", as used herein, refers to the wavelength at which the emission spectrum of a label reaches a maximum. For example, a label that is referred herein as red has an emission spectrum with a maximum at about 650 nm.

As used herein, the term "data" refers to refers to a collection of organized information, generally derived from results of experiments in lab or in silico, other data available to one of skilled in the art, or a set of premises. Data may be in the form of numbers, words, annotations, or images, as measurements or observations of a set of variables. Data can be stored in various forms of electronic media as well as obtained from auxiliary databases.

As used herein, the term "single nucleotide polymorphism", or "SNP" for short, refers to a phenomenon in which two or more alternative alleles (i.e., different nucleotides) are present at a single nucleotide position in a genomic sequence at appreciable frequency (e.g., often 1%) in a population. In some cases, SNPs may be present at a frequency less than 1% in a population. As used herein, the term SNP may include these "rare SNPs" (present at a frequency less than 1% in a population) or even "single nucleotide variants" (SNVs) that have only been detected in one or a few samples to date.

As used herein, the term "SNP site" denotes the position of a SNP in a genomic sequence. A SNP site may be indicated by genomic coordinates. The nucleotide sequences of hundreds of thousands of SNPs from humans, other mammals (e.g., mice), and a variety of different plants (e.g., corn, rice and soybean), are known (see, e.g., Riva et al 2004, *A SNP-centric database for the investigation of the human genome* BMC Bioinformatics 5:33; McCarthy et al 2000 *The use of single-nucleotide polymorphism maps in pharmacogenomics* Nat Biotechnology 18:505-8) and are available in public databases (e.g., NCBI's online dbSNP database, and the online database of the International HapMap Project; see also Teufel et al 2006 *Current bioinformatics tools in genomic biomedical research* Int. J. Mol. Med. 17:967-73).

As used herein, the term "SNP sequence" refers to is a naturally-occurring nucleotide sequence that contains a SNP site. Since at least two alleles my exist at a given SNP site, at least a pair of SNP sequences correspond to each SNP site, both of which contain the same flanking sequences, but the nucleotide at the SNP site differ. A SNP sequence can be of any length, and in particular embodiments may be up to 5, 10, 15, 20, 25, 30, 35 or 40 nucleotides or more, e.g., up to 50-80 nucleotides or more. In particular embodiments, the sequences that flank a SNP site on either side may be at least 2, 3, 4, 5, 6, 7, 8, 9, 10, 11, 12, 13, 14, 15, 16, 17, 18, 19, 20 nucleotides long, or more, e.g., 15-30 or 15-40 nt, or any range in between (such as 3-15, 5-12, 9-16, etc.).

As used herein, the term "SNP allele" refers to the identity of the nucleotide at a SNP site (e.g., whether the SNP site has a G, A, T or C or a deletion or insertion or a small number of nucleotides). A "first allele" and a "second allele" of a SNP are different alleles, i.e., they have different nucleotides at the SNP site.

As used herein, the term "restriction enzyme" refers to a site-specific endonuclease that cuts double stranded DNA at a specific nucleotide sequence. Restriction enzyme recognize and cut within specific nucleotide sequences in double-stranded DNA. A restriction enzyme may cleave double stranded DNA to produce blunt ends or sticky ends that may have a 3' or 5' overhang of 1, 2, 3, or 4 nucleotides, for example. In some cases, a restriction enzyme may cleave a sequence that lies outside the recognition sequence for that enzyme, for example, a specific number of nucleotides away from the recognition site. TypeIIS, TypeIIG, and TypeIII restriction enzymes represent examples of classes of restriction enzymes that cleave outside of their recognition sequence, and which may be used in embodiments. Further information on TypeIIS, TypeIIG, and TypeIII restriction enzymes may be found in the REBASE restriction enzyme database at the NEB website.

The term "cleavage site" generally refers to the phosphodiester bond between two adjacent nucleotides that is cleaved by a restriction enzyme. As used herein, "cleavage site" can also refer to the site that is not cut in one allele but is cut in the other depending on the allele of the SNP. The site that is cleaved for a sequence with the cut allele is the cleavage site. The analogous site for which the bases surrounding the SNP base are the same as the uncut allele is also referred to herein as the cleavage site.

For some enzymes, the cleavage site is within the recognition site, or one of the recognition sites, for the enzyme. For other enzymes, e.g., TypeIIS enzymes, this cleavage site is offset from the recognition site. The SNP will be detectable by this method if the SNP occurs within the recognition site, independently of the offset between the cleavage site and the SNP site.

The term "recognition site" is the sequence of nucleotides recognized by a restriction enzyme. The recognition site for a restriction enzyme may be in the range of 4-8 or more base pairs in length. In certain cases, a recognition site may be 4, 5 or 6 base pairs in length. Restriction enzymes that cut within their recognition site as well restriction enzymes that cut outside of their recognition site (e.g., Type IIA, Type IIB, Type IIS, and Type IIG restriction enzymes) may be employed herein.

If a restriction enzyme cleaves a sequence containing a SNP "only if a first allele of a SNP is present", the restriction enzyme cleaves at a cleavage site only if a first allele of the SNP is present and not if a different (i.e., second) allele of the SNP is present. In such cases, the SNP site is part of the recognition site of the restriction enzyme. If the recognition site of a restriction enzyme contains a SNP site, the restriction enzyme may or may not cleave at that recognition site, depending on the allele of the SNP at that site. As noted above, in certain cases a restriction enzyme that cuts outside of its recognition site may be employed herein. In these embodiments, the enzyme will cleave upstream or downstream of the SNP site, only if a first allele of the SNP is present. As used herein, a "digestable SNP site" refers to a restriction enzyme recognition site comprising a SNP, such that the restriction enzyme cleaves the cleavage site only if a first allele of the SNP is present.

As used herein, the term "a probe that spans a cleavage site" and grammatical equivalents thereof is a probe that hybridizes to contiguous nucleotides of a sequence that contains a cleavage site, including sequence on both sides of a cleavage site. In one embodiment, such a probe bases pairs with at least 6 base pairs immediately 3' to the cleavage site and at least 6 base pairs immediately 5' of the cleavage site. Such a probe may or may not base pair with the nucleotide at the SNP site, depending on the allele of the SNP. A probe that spans a cleavage site may hybridize to, for example, 10-35, e.g., 15-30 nucleotides of flanking sequence on both sides of the cleavage site. This definition defines what is excluded by the term "a probe that does not span a cleavage site" and grammatical equivalents thereof.

The term "end-labeling" as used herein refers to the addition of a label to one or both ends of a nucleic acid. The 5' and/or 3' ends of a nucleic acid strand may be end-labeled. A nucleic acid may be end-labeled by ligation (i.e., using a ligase to add a labeled oligonucleotide) or by polymerization (e.g., using a polymerase or terminal transferase to add labeled nucleotides, for example). In addition to referring to the addition of a label that is directly detectable (e.g., a fluorescent label), the term "end-labeling" also refers to the addition of a label that is indirectly detectable. In this context, "end-labeling" explicitly encompasses "sequence tagging" methods in which an adaptor is ligated to a nucleic acid, where the ligated adaptor facilitates detection of the adaptor-ligated nucleic acid, e.g., by hybridization. Such sequence tagging methods may be done by ligating a single or double stranded oligonucleotide, which may be 15-50 nucleotides (e.g, 15-40 nucleotides) in length onto the ends of a nucleic acid. In some embodiments, both strands of a DNA molecule are labeled with the same label. In other embodiments, the two strands are labeled with different labels.

DESCRIPTION OF EXEMPLARY EMBODIMENTS

Before the present invention is described in greater detail, it is to be understood that this invention is not limited to particular embodiments described, and as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It must be noted that as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Method of Genome Analysis

As noted above, a method for analyzing a sequence comprising a SNP site is provided. In general terms, the method comprises: a) contacting a first DNA sample with a first restriction enzyme to provide DNA fragments, wherein: i) the first restriction enzyme cleaves the sequence at a cleavage site only if a first allele of a SNP is present at the SNP site; b) end-labeling the DNA fragments to produce an end-labeled sample; c) hybridizing the end-labeled sample to an array comprising a probe sequence that: i) hybridizes to an end-labeled polynucleotide of the end-labeled sample; ii) hybridizes to a fragment produced if the first restriction enzyme cleaves the sequence at the SNP site; and iii) does not span the cleavage site; d) comparing the amount of hybridization between the digested sample and the probe sequence to a reference signal, and e) determining whether the first allele of the SNP is present in the DNA sample, wherein the relative hybridization of the digested sample to the probe as compared to the reference signal indicates whether the first allele of the SNP is present in the DNA sample.

In certain embodiments, the method involves contacting a sample comprising double-stranded genomic DNA (which may be fragmented genomic DNA) with a restriction enzyme (e.g., an enzyme that has a recognition site of four, five, six or more bases) under conditions suitable for the enzyme to cleave the DNA. RsaI or AluI are examples of suitable restriction enzymes, although any other suitable enzyme may be employed. In certain embodiments, the cleavage site may not lie within the recognition site of the restriction enzyme. Cleavage of the cleavage site by the enzyme is dependent on the allele of the SNP. If the enzyme cleaves at the cleavage site then the site contains a first allele of the SNP, and if the enzyme does not cleave at the cleavage site then the site contains a second allele of the SNP. Whether a cleavage site is cleaved or uncleaved by the restriction enzyme can be determined by the method described below. In this method, the ends of the fragments are modified by either attaching a tag sequence or a fluorescent label, for example. The tag sequence or label enables detection of a gain in signal after hybridization to an array probe if the target DNA is cut by the restriction enzyme.

A first embodiment of the subject method is schematically illustrated in FIG. 1. In this embodiment, the end-labeling step comprises ligating an adapter to the DNA fragments and the hybridizing step comprises hybridizing the end-labeled sample to a microarray comprising a probe that spans the junction between the adaptor and a polynucleotide fragment in the end-labeled sample. In this embodiment, an adapter is ligated to the cut ends, and the ligation products are hybridized to an array containing a probe that: a) spans the junction between the fragments and the adaptor and b) is designed so that ligated products hybridize more efficiently than undigested or unligated products. In this embodiment, the genomic DNA may be digested with a restriction enzyme to provide "sticky ends" (i.e., a 5' or 3' overhang such as a 2, 3 or 4 bp overhang) that may be ligated to an adapter sequence that hybridizes to the overhang and can be ligated to the recessed nucleotide of the cleavage site. Alternative, the enzyme may provide blunt ends, as shown in FIG. 1.

Figure 2:
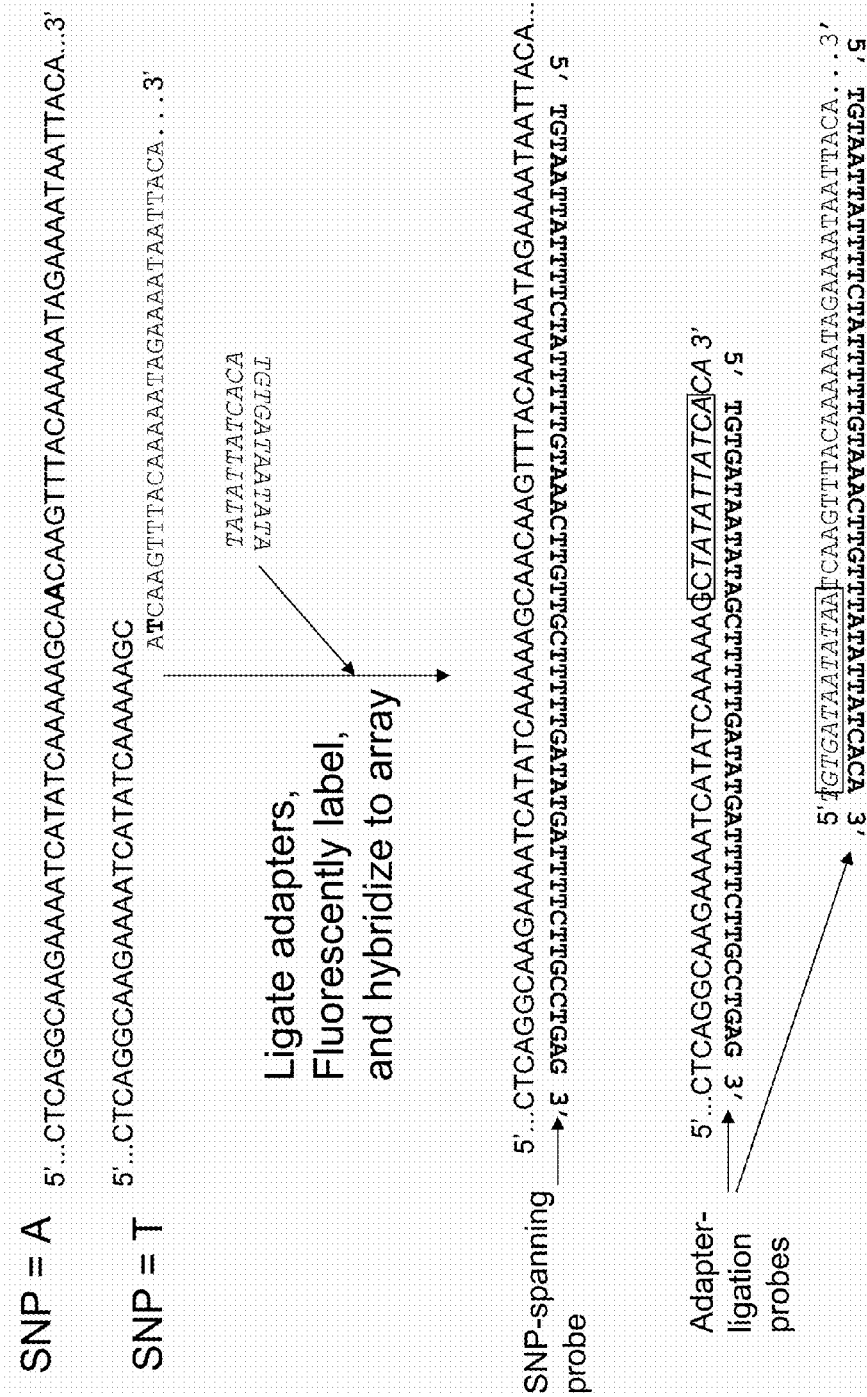
FIG. 2 schematically illustrates an embodiment of a method using exemplary sequences. From top to bottom: SEQ ID NOS: 13-23.

Rather than performing PCR using a primer that hybridizes to the adaptor sequence, ligated adapter sequence can be detected by hybridization to a probe of an array. As shown in FIG. 1, the array probe can be designed to hybridize to the junction between the adapter and the cleavage-site-adjacent sequence, as well as sequences that flank the junction (e.g., at least 15 to 30 nucleotides on both sides of the junction). As shown in FIG. 1, the array probe and the adapter sequence can be designed to ensure that neither the uncut target DNA (i.e., DNA that has not been ligated to the adapter) nor unrelated sequences (i.e., sequences that do not flank the SNP site that are nevertheless digested and ligated to adaptor) will hybridize efficiently to the probe. In certain embodiments, the ligated product may hybridize to the probe with a Tm that is at least 10° C. higher (e.g., at least 15° C. higher, at least 20° C. higher, up to 30° C. higher, or more) than other products (which may be either uncleaved or of unrelated sequence), thereby allowing ligated products to be discriminated from other products by hybridization under stringent conditions. The sample may be fluorescently labeled at any point prior to hybridization to the array probe. In this embodiment, the fragments are end-labeled in that an adaptor is added to the end of the fragments, and hybridization of the adaptor ligated fragments may be detected by a directly detectable label attached to, for example, one or more nucleotides at any position in the fragment. An example of this method using specific sequences is illustrated in FIG. 2.

Methods for designing probes that may be employed in this method can be adapted from those described in detail in a U.S. Patent Application Pub. No. 20090035762 and U.S. patent application Ser. No. 12/541,032, the disclosures of which is incorporated herein by reference for disclosure of those methods and the general characteristics of such probes. In general terms, such a probe may be 25-70 nucleotides in length (e.g., 30-60 nucleotides in length) and the nucleotides that base pair with the nucleotides that are immediately adjacent to the adaptor/fragment junction may be within about 10 or 15 nucleotides of the center of the probe. The sequences flanking the nucleotides that base pair with the junction may be Tm balanced in that they similar Tms, e.g., have Tms that are within 5° C. of one another. The probe may be complementary to a first or a second allele of the SNP, or there may be a base deletion at a position that corresponds to the SNP site, for example, depending on how the probe is designed. In particular embodiments, cleavage of the sequence at the cleavage site by the first restriction enzyme and subsequent ligation results in more hybridization of the sample to the probe relative to a sample in which the sequence is not digested by the first restriction enzyme, thereby producing more signal.

Figure 3:
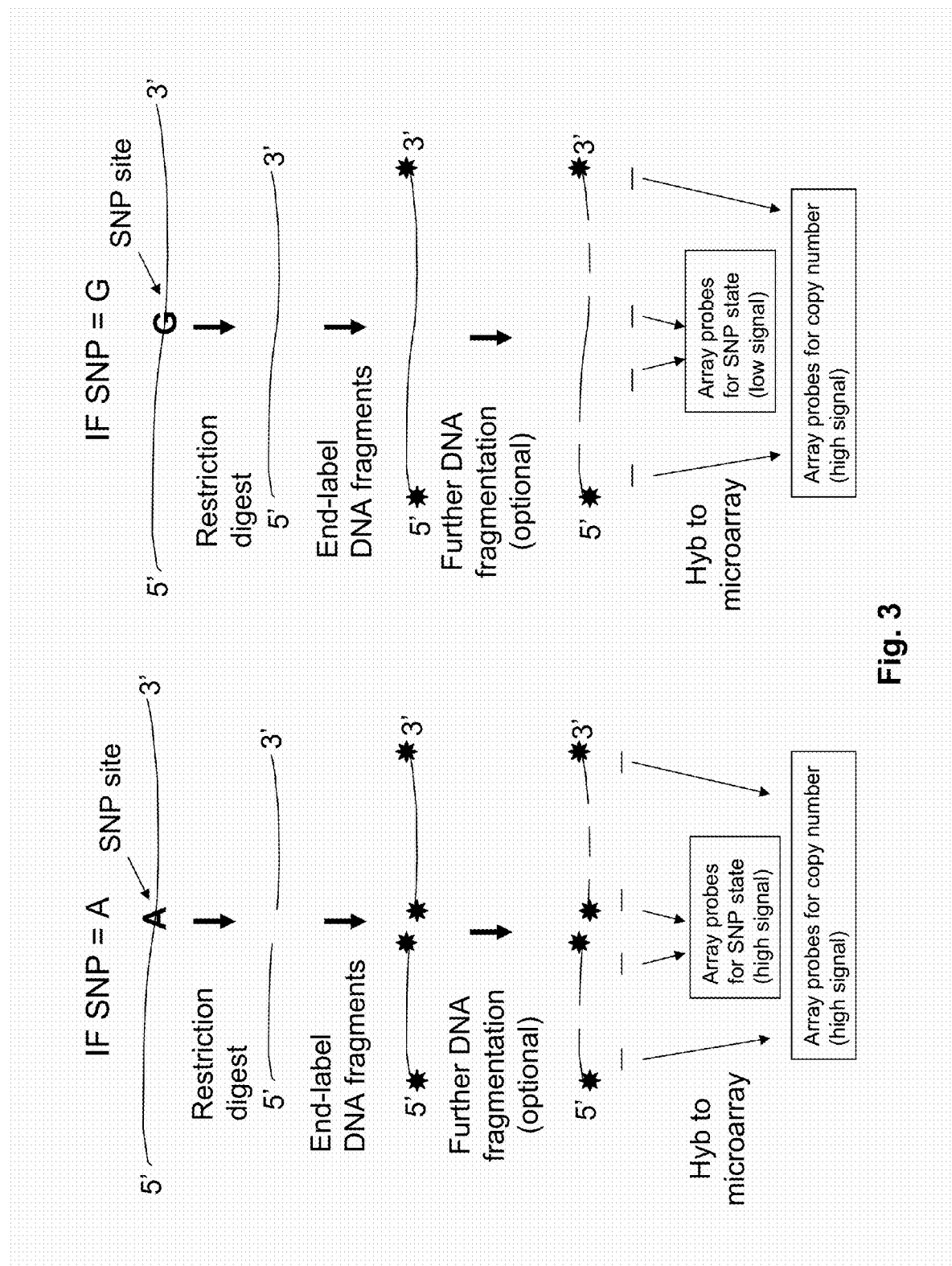
FIG. 3 schematically illustrates one embodiment in which the allele of a SNP is determined using a protocol in which a restriction enzyme cleavage site is end-labeled with a fluorescent label.

A second embodiment of the subject method is schematically illustrated in FIG. 3. In this embodiment, the sample is first digested then end-labeled by, for example, enzymatic addition of a fluorescent nucleotide to the ends of the digested nucleic acid. Following labeling, the labeled nucleic acid may be further fragmented (e.g., digested with another enzyme or mechanically fragmented), and then hybridized to an array containing probes that are proximal to the cleavage site (e.g., within 50 or 100 bases of the cleavage site). As illustrated in FIG. 3, cleavage sites that are cleaved by the restriction enzyme and subsequently labeled are detected. Cleavage sites that are not cleaved by the restriction enzyme are not labeled and are not detected. In particular embodiments and as illustrated in FIG. 3, the array may also contain probes for sequences that are distal to the cleavage site (but still on the same fragment as the proximal probe sequences), thereby allowing the copy number of the fragment containing the SNP site to be determined.

In this embodiment, an enzyme may be employed to attach one or more fluorescently labeled nucleotides to the cut ends of the target DNA. Several labeling methods are available. For example, if the target DNA is cut with an enzyme that leaves a 3' overhang, a fluorescent nucleotide could be added to the 3' overhang with terminal deoxytransferase (TdT). Use of dye-terminator nucleotides would ensure that only one fluorescent label is added. Alternatively, if the target DNA is cut with an enzyme that leaves a 5' overhang, one or more fluorescent nucleotides can be added to the 3' end using a DNA polymerase, e.g., Klenow. Finally, if the target DNA is cut with an enzyme that produces blunt ends, one or more fluorescent nucleotides could be added with a DNA polymerase that catalyzes terminal additions such as Taq polymerase. In this embodiment and as illustrated in FIG. 3, the end-labeling step may comprise: i) adding a labeled nucleotide to the end of the DNA fragments to produce a population of labeled polynucleotides; and ii) fragmenting the population of labeled polynucleotides to produce the end-labeled sample. In particular embodiments, the fragmenting may be done enzymatically, mechanically or chemically, for example.

As shown in FIG. 3, after the cut ends are fluorescently labeled, hybridization of the end-labeled fragments can be measured using probes of an array. In certain cases, the DNA in the sample may also be labeled with a second label that is distinguishable from the end label. For example, the ends of the DNA can be labeled with Cy5, and the fragments can be bulk labeled with Cy3, e.g., using Agilent's Genomic DNA ULS Labeling Kit, for example. In this case, one sample could be visualized on a two-color array, where the one channel provides copy-number information and the other channel provides SNP information. In embodiments in which a ULS labeling protocol is employed, the labeled DNA may be further fragmented by chemical treatment, which will ensure that there is only one end-label per fragment.

Means of attaching labels to nucleic acids are well known to those of skill in the art and include, for example nick translation or end-labeling, by kinasing of the nucleic acid and subsequent attachment of a nucleic acid linker joining the oligonucleotides to a label. In certain embodiments, the nucleic acid may be labeled by Universal Linkage System (ULS™, KREATECH Diagnostics). In brief, ULS™ labeling is based on the stable binding properties of platinum (II) to nucleic acids. The ULS molecule consists of a monofunctional platinum complex coupled to a detectable molecule of choice. Standard methods may be used for labeling the oligonucleotide, for example, as set out in Ausubel, et al, (*Short Protocols in Molecular Biology,* 3rd ed., Wiley & Sons, 1995) and Sambrook, et al, (*Molecular Cloning: A Laboratory Manual, Third Edition,* (2001) Cold Spring Harbor, N.Y.).

In a particular embodiment, the reference sample may contain one or more known alleles of the SNP at the SNP site and has been contacted with the first restriction enzyme. In another embodiment, the reference sample may be a second portion of the DNA sample that has not been contacted with the first restriction enzyme. In a further embodiment, the reference sample may comprise a pooled plurality of genomic DNA samples from different subjects, thereby "averaging" out the SNP status of the population. The labeled digested sample and the labeled reference sample may be co-hybridized to the same array, or hybridized to different arrays. In another embodiment, the signal strength for one copy, two copies and three copies or more may be known by statistical analysis of data obtained from other probes (e.g., probes in the same genomic region as the SNP.) As such, in this embodiment, the allele of the SNP present at the SNP site may be determined by comparing the signal from the probe used to ranges of values that are predicted to define each of the SNP alleles. In another embodiment, the reference sample may comprise a library of data from multiple samples with different SNP alleles, such that signals from a particular array probe may fall into classes (e.g., low, medium, high signals) corresponding to different SNP alleles. In this embodiment, the exact sequence of the SNP alleles in the individual samples in the library may be unknown.

In some embodiments, the method may further comprise determining whether the DNA sample is homozygous or heterozygous for the first allele of the SNP, and in further embodiments, the method may further comprise determining the copy number of the fragment containing the SNP. In embodiments, a the allelic state of a plurality of SNPs in a genomic region may be determined, and loss-of-heterozygosity (LOH) analysis may be performed. In this way, conditions such as uniparental disomy (UPD) may be detected.

Figure 4:
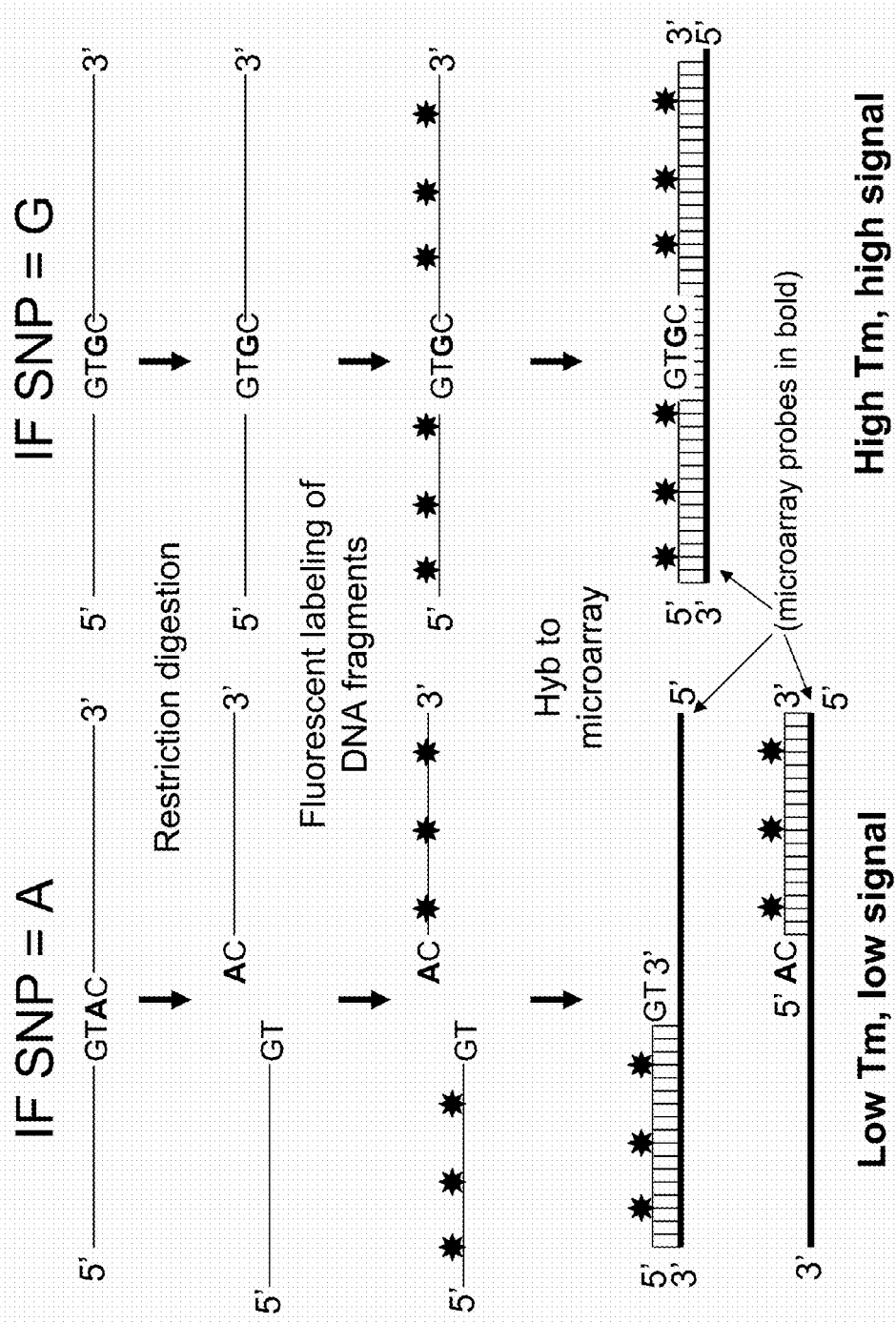
FIG. 4 schematically illustrates a method that may be combined with the subject method.

The method described above may be combined with the method described in U.S. Patent Application Pub. No. 20090035762, which is generally illustrated in FIG. 4, to provide an orthogonal analysis of a SNP site, without impacting the accuracy of the method described in U.S. Patent Application Pub. No. 20090035762 and illustrated in FIG. 4. U.S. Patent Application Pub. No. 20090035762 is incorporated herein for disclosure of the details of the method illustrated in FIG. 4, including exemplary probe design protocols, sample preparation protocols, sample labeling protocols, and data analysis protocols. FIG. 4 generally provides a method of sample analysis that comprises: a) contacting a first DNA sample comprising genomic DNA with a first restriction enzyme to provide a digested sample, wherein: i) the DNA sample may comprise a sequence comprising a SNP site; and ii) the first restriction enzyme cleaves the sequence only if a first allele of a SNP is present at the SNP site; b) hybridizing the digested sample to a microarray comprising a probe sequence that is complementary to the sequence comprising the cleavage site; c) comparing the amount of hybridization between the digested sample and the probe sequence to the amount of hybridization between a reference sample and the probe sequence, and d) determining whether the first allele of the SNP is present in the DNA sample, wherein the relative hybridization of the digested sample to the probe as compared to the reference sample indicates whether the first allele of the SNP is present in the DNA sample. As illustrated, cleavage of the sequence at the cleavage site by the first restriction enzyme results in less hybridization of the digested sample relative to a sample in which the sequence is undigested.

In the method illustrated in FIG. 4, array probes spanning the cleavage site are used to measure the amount of uncleaved DNA at a cleavage site. If the cleavage site is cut by the restriction enzyme site, a loss of signal is detected. Therefore, hybridization to the uncut DNA to a probe is measured, and the amount of cut DNA is deduced from the loss of signal. By combining the method described in FIG. 4 with an additional end-labeling step and additional array probes, as described above, the amount of cut DNA can be measured directly. As illustrated in FIG. 5, the end-labeled sample will provide a higher signal when the genomic sample is cut, and a lower signal when the DNA is uncut. Because the signal levels of the cleavage-spanning and the end-label probes are reversed for a given SNP, the assay may be more robust to conditions which disproportionately affect low or high signals (such as high background, or spurious signals caused by GC-rich sequences).

In particular embodiments and as noted above, the instant method may be performed in parallel with the method illustrated in FIG. 4, adding a different, independent, detection method for the same SNP sequence in that the levels of cut DNA and uncut DNA can be measured on distinct probes on an array, which may lead to a higher level of accuracy of SNP calls relative to any single method employed on its own. As such, in particular embodiments, the method may further comprise: a) hybridizing the digested sample to a microarray comprising a second probe sequence that is complementary to the sequence comprising the cleavage site; b) comparing the amount of hybridization between the digested sample and the second probe sequence to the amount of hybridization between a reference sample and the second probe sequence, and c) determining whether the first allele of the SNP is present in the DNA sample, wherein the relative hybridization of the digested sample to the first and second probe as compared to the reference sample indicates whether the first allele of the SNP is present in the DNA sample.

In certain embodiments and as noted above, the subject method further includes measuring copy numbers of specific nucleotide sequences in combination with determining the SNP based on the embodiments described above. In certain cases, the analysis of copy number may also be carried out using the same array, where the hybridization signals of a sample are also used to calculate copy number of sequences in the genomic sample. Additional features may be optionally included on the array to facilitate the analysis. Methods and composition used for assessing copy numbers are described in detail in U.S. Patent Application Pub. Nos. 20070238106 and 20070238108, disclosures of which are incorporated herein by reference.

As noted previously, the subject method involves the digestion of a double-stranded DNA in a genomic sample. The genomic DNA may undergo staining, shearing, fragmentations, purification, etc., prior to being contacted with the restriction enzyme in the method.

The labeling step may incorporate a detectable label into a nucleic acid so hybridization to an array of probes may be measured. Detectable labels are known in the art and need not described in detail herein. Briefly, exemplary detectable components include radioactive isotopes, fluorophores, fluorescence quenchers, affinity tags, e.g. biotin, crosslinking agents, chromophores, colloidal gold particles, beads, quantum dots, etc. In certain embodiments, the detectable label, such as biotin, may require incubation with a recognition element, such as streptavidin, or with secondary antibodies to yield detectable signals. In other embodiments, the detectable label, such as a fluorophore, may be detected directly without performing additional steps.

Additional fluorescent dyes of interest include: xanthene dyes, e.g. fluorescein and rhodamine dyes, such as fluorescein isothiocyanate (FITC), 6-carboxyfluorescein (commonly known by the abbreviations FAM and F), 6-carboxy-2',4',7',4,7-hexachlorofluorescein (HEX), 6-carboxy-4',5'-dichloro-2',7'-dimethoxyfluorescein (JOE or J), N,N,N',N'-tetramethyl-6-carboxyrhodamine (TAMRA or T), 6-carboxy-X-rhodamine (ROX or R), 5-carboxyrhodamine-6G (R6G5 or G5), 6-carboxyrhodamine-6G (R6G6 or G6), and rhodamine 110; cyanine dyes, e.g. Cy3, Cy5 and Cy7 dyes; coumarins, e.g umbelliferone; benzimide dyes, e.g. Hoechst 33258; phenanthridine dyes, e.g. Texas Red; ethidium dyes; acridine dyes; carbazole dyes; phenoxazine dyes; porphyrin dyes; polymethine dyes, e.g. cyanine dyes such as Cy3, Cy5, etc; BODIPY dyes and quinoline dyes. Specific fluorophores of interest that are commonly used in subject applications include: Pyrene, Coumarin, Diethylaminocoumarin, FAM, Fluorescein Chlorotriazinyl, Fluorescein, R110, Eosin, JOE, R6G, Tetramethylrhodamine, TAMRA, Lissamine, ROX, Napthofluorescein, Texas Red, Napthofluorescein, Cy3, and Cy5, etc. (Amersham Inc., Piscataway, N.J.), Quasar 570 and Quasar 670 (Biosearch Technology, Novato Calif.), Alexafluor555 and Alexafluor647 (Molecular Probes, Eugene, Oreg.), BODIPY V-1002 and BODIPY V1005 (Molecular Probes, Eugene, Oreg.), POPO-3 and TOTO-3 (Molecular Probes, Eugene, Oreg.), and POPRO3 TOPRO3 (Molecular Probes, Eugene, Oreg.). Further suitable distinguishable detectable labels may be found in Kricka et al. (*Ann Clin Biochem.* 39:114-29, 2002).

In certain cases, the DNA under study may be stained with a nonspecific label, such as an intercalating fluorescent dye or other dyes that would label DNA in a non-sequence specific manner (e.g. DAPI, Hoechst, YOYO-1, YO-PRO-1, or PicoGreen).

The present disclosure also provides an array to carry out the subject method. The array contains probes for carrying out the method. In one embodiment, the array may contain a plurality of probes that each contain a first sequence (e.g., 15 to 30 nucleotides) that flanks a digestable SNP site in a mammalian genome, and, immediately adjacent to that sequence, a second sequence that hybridizes to an adaptor. Collectively, one end of the probes on the array has the same sequence (which hybridizes to the adaptor) and the other end of the probes have sequences that are different to one another. In other embodiments, the probes may be designed to hybridize to sequences that flank a digestable SNP site in a mammalian genome. In certain embodiments, there may be at least 5,000, at least 10,000, at least 100,00 or at least 100,000 or more of such probes on an array. The array may also contain SNP spanning probes as described in U.S. Patent Application Pub. No. 20090035762.

In certain embodiments, the probes are designed such that duplexes formed by hybridization to the probes are $T_m$-matched. In some embodiments, the array contains duplicates of probes. In some embodiments, the array may contain multiple sets (e.g, at least 10, at least 100, at least 1,000, at least 10,000 or at least 50,000 or more sets) of probes, where each set of probes is designed for analysis of a single SNP site and may contain as few as two and as many as 4 or 8 probes.

Reading of the array may be accomplished by illuminating the array and reading the location and intensity of resulting fluorescence at each feature of the array to detect any binding complexes on the surface of the array. For example, a scanner may be used for this purpose that is similar to the AGILENT MICROARRAY SCANNER available from Agilent Technologies, Palo Alto, Calif. Other suitable apparatus and methods are described in U.S. Pat. No. 7,205,553 "Reading Multi-Featured Arrays" by Dorsel et al.; and U.S. Pat. No. 7,531,303 "Interrogating Multi-Featured Arrays" by Dorsel et al., both disclosures of which are incorporated herein by reference. However, arrays may be read by any other method or apparatus than the foregoing, with other reading methods including other optical techniques (for example, detecting chemiluminescent or electroluminescent labels) or electrical techniques (where each feature is provided with an electrode to detect hybridization at that feature in a manner disclosed in U.S. Pat. No. 6,221,583 and elsewhere). Results from the reading may be raw results (such as fluorescence intensity readings for each feature in one or more color channels) or may be processed results such as obtained by rejecting a reading for a feature which is below a predetermined threshold and/or forming conclusions based on the pattern read from the array (such as whether or not a particular target sequence may have been present in the sample or an organism from which a sample was obtained exhibits a particular condition). The results of the reading (processed or not) may be forwarded (such as by communication) to a remote location if desired, and received there for further use (such as further processing).

In certain embodiments, the subject methods include a step of transmitting data from at least one of the detecting and deriving steps, as described above, to a remote location. By "remote location" is meant a location other than the location at which the array is present and hybridization occur. For example, a remote location could be another location (e.g. office, lab, etc.) in the same city, another location in a different city, another location in a different state, another location in a different country, etc. As such, when one item is indicated as being "remote" from another, what is meant is that the two items are at least in different buildings, and may be at least one mile, ten miles, or at least one hundred miles apart. "Communicating" information means transmitting the data representing that information as electrical signals over a suitable communication channel (for example, a private or public network). "Forwarding" an item refers to any means of getting that item from one location to the next, whether by physically transporting that item or otherwise (where that is possible) and includes, at least in the case of data, physically transporting a medium carrying the data or communicating the data. The data may be transmitted to the remote location for further evaluation and/or use. Any convenient telecommunications means may be employed for transmitting the data, e.g., facsimile, modem, internet, etc.

As noted above, the subject method involves comparing the data derived from a genomic DNA sample to a reference. The reference may also undergo the subject method in the same way as the genomic sample under interest. In other cases, the reference sample is contacted to an array to provide hybridization signals as a control. The reference sequence may be a sequence derived from an identified source or from the same species as the genomic sample under study. The source of the reference may be known to be homozygous or heterozygous for a particular genomic locus of interest. In certain cases, the source may be wild-type for a genomic locus of interest. The source may contain an allelic variant of interest. In certain cases, the reference sequence may be known so that the alleles of the single nucleotide polymorphisms are known.

Kits

Also provided by the present disclosure are kits for practicing the subject method as described above. The subject kit contains reagents for performing the method described above and in certain embodiments may contain a restriction enzyme, end-labeling reagents (which may include an adaptor, a ligase, a polymerase and/or a fluorescent nucleotide), etc. as described above, an array, and an optional reference sample.

In addition to above-mentioned components, the subject kit may further include instructions for using the components of the kit to practice the subject method. The instructions for practicing the subject method are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

In addition to the instructions, the kits may also include one or more control analyte mixtures, e.g., two or more control analytes for use in testing the kit.

In addition to above-mentioned components, the subject kit may include software to perform comparison of a collected hybridization signal with another.

Utility

The subject method finds use in a variety of applications, where such applications generally include nucleic acid detection applications in which the presence of a particular nucleotide sequence in a given sample is detected at least qualitatively, if not quantitatively. In general, the above-described method may be used in order to determine the allele of a SNP in a genomic DNA.

Since digestion is sequence dependent, the presence or absence of digestion in specific locations on double-stranded DNA and their levels of hybridization to their respective probes are informative of the identity of the allele at a SNP site. By comparing the level of hybridization of a sample to that of a control sample, the identity of the SNP allele may be determined. In some cases, the genotype of the SNP locus may also be determined based on the ratio of hybridization signals from two samples, as described previously.

Other assays of interest which may be practiced using the subject method include: genotyping, scanning of known and unknown mutations, gene discovery assays, genomic structural mapping, loss-of-heterozygosity analysis, paternity testing, differential gene expression analysis assays, nucleic acid sequencing assays, sample identity, disease diagnosis and prognosis, and the like.

The data of SNP alleles identified through the use of the subject method can be collected and compared to a set of known SNPs associated with a disease or biological condition with the purpose of identifying an unknown source, genotyping, predicting a biological condition. This might represent comparison between SNPs coming from variants of a region to a reference. Identification of one or more SNPs in a sample genome may be useful for a wide variety of investigations, such as identifying origin of a crop, identifying species of fish or other animals, identifying pathogens, diagnosing human diseases, investigating cancer lineages or distinguishing between a finite number of known genotypes, etc.

In certain cases, the genomic sample under study may be derived from a sample tissue suspected of a disease or infection. Performing the subject method to analyze the genomic sample from such sample tissues would be useful for disease diagnosis and prognosis. Patents and patent applications describing methods of using arrays in various applications include: U.S. Pat. Nos. 5,143,854; 5,288,644; 5,324,633; 5,432,049; 5,470,710; 5,492,806; 5,503,980; 5,510,270; 5,525,464; 5,547,839; 5,580,732; 5,661,028; 5,800,992; the disclosures of which are herein incorporated by reference.

Since the nucleotide sequences of hundreds of thousands of SNPs from humans, other mammals (e.g., mice), and a variety of different plants (e.g., corn, rice and soybean), are known (see, e.g., Riva et al 2004, *A SNP-centric database for the investigation of the human genome* BMC Bioinformatics 5:33; McCarthy et al 2000 *The use of single-nucleotide polymorphism maps in pharmacogenomics* Nat Biotechnology 18:505-8) and are available in public databases (e.g., NCBI's online dbSNP database, and the online database of the International HapMap Project; see also Teufel et al 2006 *Current bioinformatics tools in genomic biomedical research* Int. J. Mol. Med. 17:967-73), choosing an enzyme and designing probes should be well within the skill of one of skilled in the art.

The above described applications are merely representations of the numerous different applications for which the subject array and method of use are suited. In certain embodiments, the subject method includes a step of transmitting data from at least one of the detecting and deriving steps, as described above, to a remote location. By "remote location" is meant a location other than the location at which the array is present and hybridization occur. For example, a remote location could be another location (e.g., office, lab, etc.) in the same city, another location in a different city, another location in a different state, another location in a different country, etc. As such, when one item is indicated as being "remote" from another, what is meant is that the two items are at least in different buildings, and may be at least one mile, ten miles, or at least one hundred miles apart. "Communicating" information means transmitting the data representing that information as electrical signals over a suitable communication channel (for example, a private or public network). "Forwarding" an item refers to any means of getting that item from one location to the next, whether by physically transporting that item or otherwise (where that is possible) and includes, at least in the case of data, physically transporting a medium carrying the data or communicating the data. The data may be transmitted to the remote location for further evaluation and/or use. Any convenient telecommunications means may be employed for transmitting the data, e.g., facsimile, modem, internet, etc.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method for analyzing a sequence comprising a SNP (single nucleotide polymorphism) site, comprising:
   a) contacting a first DNA sample with a first restriction enzyme to provide DNA fragments, wherein:
      i) said first restriction enzyme cleaves said sequence at a cleavage site only if a first allele of a SNP is present at said SNP site;
   b) end-labeling said DNA fragments to produce an end-labeled sample;
   c) hybridizing said end-labeled sample to an array comprising a probe sequence that:
      i) hybridizes to an end-labeled polynucleotide of said end-labeled sample;
      ii) hybridizes to a fragment produced if said first restriction enzyme cleaves said sequence at said cleavage site; and
      iii) does not span said cleavage site;
   d) comparing the amount of hybridization between the digested sample and the probe sequence to a reference signal, and
   e) determining whether the first allele of the SNP is present in the DNA sample, wherein the relative hybridization of the digested sample to the probe as compared to the reference signal indicates whether the first allele of said SNP is present in the DNA sample.

2. The method of claim 1, wherein the reference signal is the amount of hybridization between a reference sample and the probe sequence.

3. The method of claim 1, wherein:
   said end-labeling step b) comprises ligating an adapter to said DNA fragments; and
   said hybridizing step c) comprises hybridizing said end-labeled sample to an array comprising a probe that spans the junction between said adaptor and a polynucleotide fragment in the end-labeled sample.

4. The method of claim 1, wherein:
   said end-labeling step b) comprises:
      i) adding a labeled nucleotide to the end of said DNA fragments to produce a population of labeled polynucleotides; and
      ii) fragmenting said population of labeled polynucleotides;
   to produce said end-labeled sample.

5. The method of claim 4, wherein said fragmenting is done enzymatically, mechanically or chemically.

6. The method of claim 1, further comprising:
   a) hybridizing said digested sample to a microarray comprising a second probe sequence that spans said cleavage site;
   b) comparing the amount of hybridization between the digested sample and the second probe sequence to the amount of hybridization between a reference sample and the second probe sequence, and
   c) determining whether the first allele of the SNP is present in the DNA sample, wherein the relative hybridization of the digested sample to the first probe and the second probe sequences as compared to the reference sample indicates whether the first allele of said SNP is present in the DNA sample.

7. The method of claim 2, wherein said reference sample comprises one or more known alleles of the SNP at said SNP site and has been contacted with said first restriction enzyme.

8. The method of claim 2, wherein said reference sample is a second portion of said first DNA sample that has not been contacted with said first restriction enzyme.

9. The method of claim 7, wherein said reference sample comprises a plurality of DNA samples from different subjects.

10. The method of claim 3, wherein said probe is from 25 to 70 nucleotides in length, and wherein cleavage of said sequence at said cleavage site by said first restriction enzyme results in more signal relative to a sample in which said sequence is not digested by said first restriction enzyme.

11. The method of claim 10, wherein, in said probe sequence, the nucleotide corresponding to said SNP site is located within at least 10 nucleotides from the center of the probe.

12. The method of claim 1, wherein said probe sequence is complementary to sequence comprising the cleavage site, but does not comprise the SNP site.

13. The method of claim 1, wherein the probe comprises a base deletion at a position that corresponds to the SNP site.

14. The method of claim 1, further comprising determining whether said DNA sample is homozygous or heterozygous for said first allele.

15. The method of claim 1, further comprising determining the copy number of said sequence.

16. The method of claim 1, wherein the DNA sample is fragmented genomic DNA.

17. The method of claim 1, wherein the first restriction enzyme is a type IIS, type IIG or type III restriction enzyme.

18. The method of claim 1, wherein the DNA sample comprises cDNA.

19. The method of claim 2, wherein said digested sample and the reference sample are co-hybridized to the same array.

* * * * *